United States Patent
Dabney

(10) Patent No.: US 9,931,189 B2
(45) Date of Patent: *Apr. 3, 2018

(54) VETERINARY DEVICES WITH A LIGHT SOURCE AND ANTIMICROBIAL SOLUTION

(71) Applicant: Paul Dabney, Georgetown, TX (US)

(72) Inventor: Paul Dabney, Georgetown, TX (US)

(73) Assignee: Dabney Patents, L.L.C., Georgetown, TX (US)

( * ) Notice: Subject to any disclaimer, the term of this patent is extended or adjusted under 35 U.S.C. 154(b) by 543 days.

This patent is subject to a terminal disclaimer.

(21) Appl. No.: 14/583,580

(22) Filed: Dec. 26, 2014

(65) Prior Publication Data

US 2016/0015498 A1    Jan. 21, 2016

Related U.S. Application Data

(63) Continuation-in-part of application No. 14/497,269, filed on Sep. 25, 2014, now Pat. No. 9,579,177, and a continuation of application No. 14/536,633, filed on Nov. 9, 2014, now Pat. No. 9,504,848.

(60) Provisional application No. 62/026,498, filed on Jul. 18, 2014.

(51) Int. Cl.
| | |
|---|---|
| *A61N 5/06* | (2006.01) |
| *A61D 7/00* | (2006.01) |
| *A61D 9/00* | (2006.01) |
| *A61F 7/00* | (2006.01) |

(52) U.S. Cl.
CPC ................. *A61D 7/00* (2013.01); *A61D 9/00* (2013.01); *A61F 7/007* (2013.01); *A61F 7/0097* (2013.01); *A61N 5/0624* (2013.01); *A61F 2007/0071* (2013.01); *A61N 2005/063* (2013.01); *A61N 2005/0645* (2013.01)

(58) Field of Classification Search
CPC ....... A61C 19/06; A61C 19/063; A61C 1/088; A61M 5/445; A61M 25/0043; A61N 5/0616; A61N 2005/0662; A61K 33/40; A61K 31/65; A61K 31/7056; A61K 47/22; A61K 31/7048; A61K 31/203; A61K 31/60
See application file for complete search history.

(56) References Cited

U.S. PATENT DOCUMENTS

| | | | | |
|---|---|---|---|---|
| 8,439,674 | B2 * | 5/2013 | Li ................... | A61C 19/063 433/24 |
| 9,700,735 | B2 * | 7/2017 | Dabney ............. | A61N 5/062 |
| 2002/0117120 | A1 * | 8/2002 | Haze ................ | A01K 1/033 119/850 |
| 2012/0156640 | A1 * | 6/2012 | Keller .............. | A61C 19/063 433/80 |
| 2015/0066116 | A1 * | 3/2015 | Smeulders ....... | A01K 13/006 607/90 |

* cited by examiner

*Primary Examiner* — Rex R Holmes
(74) *Attorney, Agent, or Firm* — Maier & Maier, PLLC

(57) ABSTRACT

Veterinary devices with a light source and antimicrobial solution includes a solution retainer adapted to retain an antimicrobial solution against an animal; a fiber optic cable; a light termination on the fiber optic cable that provides light from the fiber optic cable to the antimicrobial solution in the solution retainer; and a light source that provides a light of a predetermined wavelength to the fiber optic cable.

15 Claims, 2 Drawing Sheets

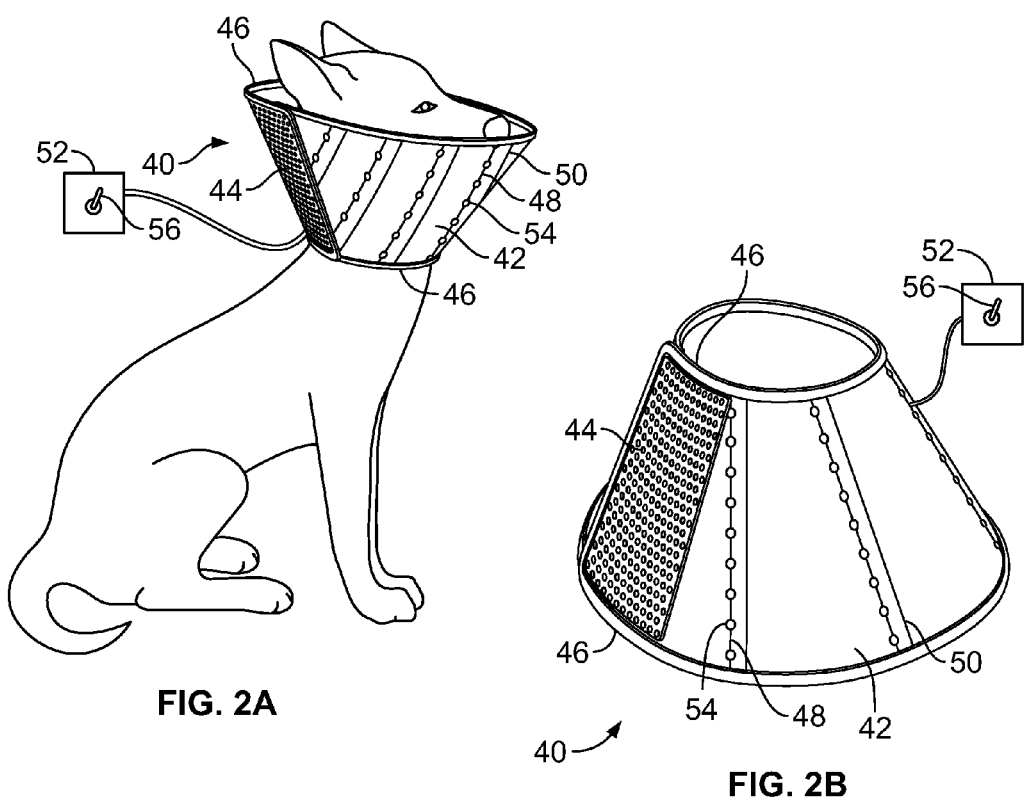
FIG. 2A
FIG. 2B
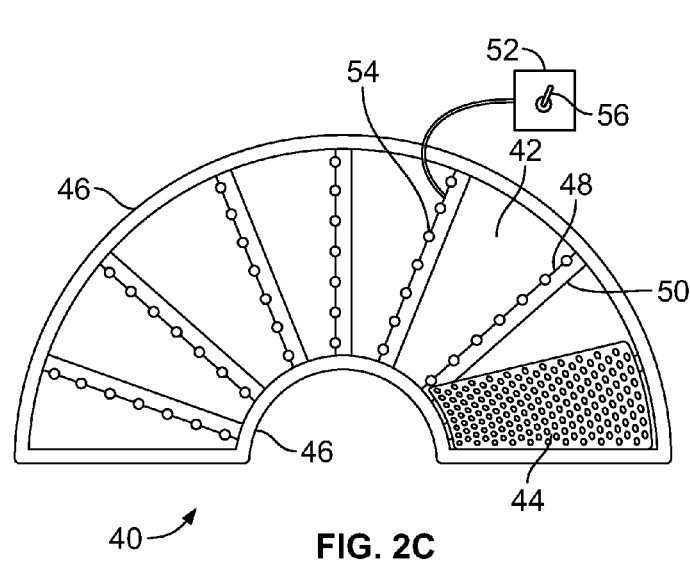
FIG. 2C

US 9,931,189 B2

VETERINARY DEVICES WITH A LIGHT SOURCE AND ANTIMICROBIAL SOLUTION

RELATED APPLICATIONS

This application claims the benefit of the filing date of U.S. Patent Application No. 62/026,498, filed Jul. 18, 2014, which is incorporated herein by reference in its entirety, U.S. Pat. No. 9,579,177 B2, filed Sep. 24, 2014, which is incorporated herein by reference in its entirety; and U.S. Pat. No. 9,504,848 B2, filed Nov. 9, 2014, which is incorporated herein by reference in its entirety.

BACKGROUND OF THE INVENTION

The present invention generally relates to enhancement of antimicrobial solutions and more specifically to veterinary devices with a light source and antimicrobial solutions.

Microbes exist that cause harm or disease in living tissues of animals.

Light of certain wavelengths has been demonstrated to improve or "super-charge" the effects of certain antimicrobial or anti-microbial agents, creating a synergistic effect to destroy or inhibit microbial growth.

Most chemical reactions work best at a certain temperature. These ideal temperatures vary for each reaction. A "scalding chart" might indicate that water of 130 degrees is safe under an exposure of 30 seconds, but over that it causes burns. Water of 120 degrees may be safe up to 5 minutes.

It would be desirable to add light of certain wavelengths to a device that holds certain antimicrobial agents in close proximity to tissues, so a synergistic effect can be created to destroy or inhibit microbial growth on the tissues.

SUMMARY OF THE INVENTION

In one aspect of the present invention, a device includes a solution retainer adapted to retain an antimicrobial solution against an animal; a fiber optic cable; a light termination on the fiber optic cable that provides light from the fiber optic cable to the antimicrobial solution in the solution retainer; and a light source that provides a light of a predetermined wavelength to the fiber optic cable.

In another aspect of the present invention, a veterinary device includes a solution retainer including a cover adapted to retain an antimicrobial solution against an animal; a fiber optic cable; a plurality of light terminations on the fiber optic cable that provides light from the fiber optic cable to the antimicrobial solution on the cover; a light source that provides a light of a predetermined wavelength to the fiber optic cable; and a heating element that warms the antimicrobial solution; wherein the fiber optic cable wraps up an inner surface of the cover so that an antimicrobial solution applied to the device is lighted with light from the cable.

BRIEF DESCRIPTION OF THE DRAWINGS

FIGS. 2A, 2B, and 2C depict another embodiment of a veterinary device according to the present invention.

DETAILED DESCRIPTION

Figure 1:
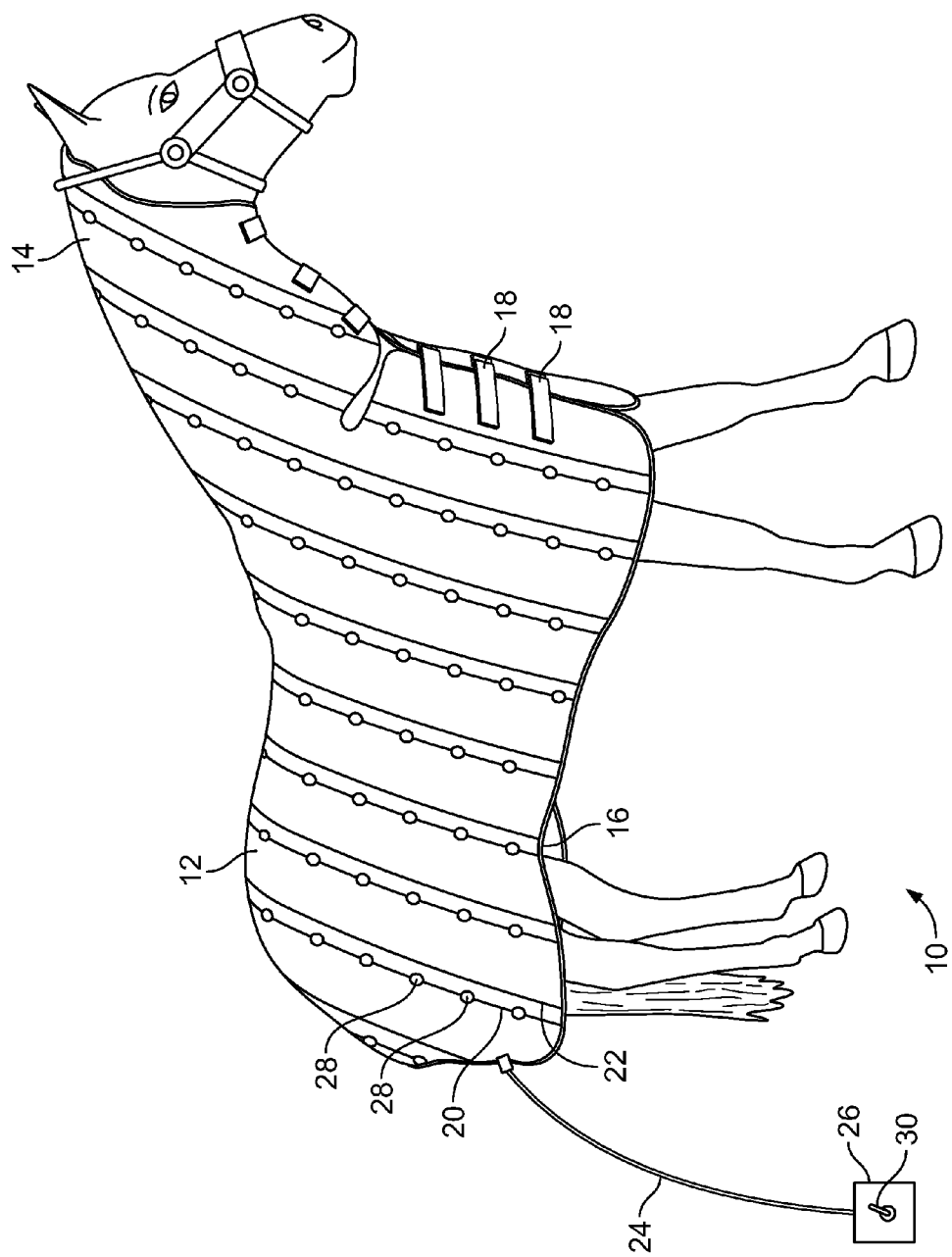
FIG. 1 depicts an embodiment of a veterinary device according to the present invention.

The preferred embodiment and other embodiments, which can be used in industry and include the best mode now known of carrying out the invention, are hereby described in detail with reference to the drawings. Further embodiments, features and advantages will become apparent from the ensuing description, or may be learned without undue experimentation. The figures are not necessarily drawn to scale, except where otherwise indicated. The following description of embodiments, even if phrased in terms of "the invention" or what the embodiment "is," is not to be taken in a limiting sense, but describes the manner and process of making and using the invention. The coverage of this patent will be described in the claims. The order in which steps are listed in the claims does not necessarily indicate that the steps must be performed in that order.

An embodiment of the present invention generally provides a device to hold solutions in contact with tissues, such as an animal's flesh, while the tissues and solutions are simultaneously being exposed to certain wavelengths of light. This device has a component that amplifies the effect of the antimicrobial solutions by using a certain wavelength of light. The antimicrobial solution may or may not be light activated at any given time. When the light is on, the solution is "supercharged" by the light. This synergistic effect eliminates or reduces more microbes than the solution acting alone.

Microbes exist that cause harm or disease in living tissues. By adding a light of certain wavelengths to a device that holds certain antimicrobial agents in close proximity to tissues, a synergistic effect can be created to destroy or inhibit microbial growth. In the oral cavity, this device could be a tray designed to cover the teeth and gingival. This tray would emit certain wavelengths of light that when combined with certain antimicrobial solutions in the tray would cause a synergistic antimicrobial effect. The light could be produced, for example, from a light emitting diode (LED) or laser. An external light source could be connected to the fiber optic cable in the solution holding apparatus with a fiber optic connection cable that may also include a fiber optic connection interface or plug.

Embodiments of the present invention may create another means to treat disease. Super charging antimicrobial solutions with certain wavelengths of lights may cause the solutions to eliminate or reduce microbes at a higher percentage than the solution alone.

Embodiments may create a synergistic effect between certain wavelengths of light and antimicrobial solutions that when applied to tissues eliminates or reduces disease causing microorganisms.

Embodiments of the present invention may consist of a solution holding apparatus or medium that emits certain wavelengths of light into the solution. When this light and solution combination is applied to tissues, a synergistic effect is created that reduces or eliminates microorganisms that cause disease. The essential components are 1. The solution holding apparatus 2. A light source 3. An antimicrobial solution.

Embodiments may utilize blue light, or another certain predetermined wavelength of light that supercharges the solution, with an exposure from a few second to minutes. Embodiments may also use an H2O2 solution, such as a gel, with concentration of 0.3 mM or any concentration of solution that is suitable as an antimicrobial agent.

In an embodiment, for safety, a "scalding chart" might indicate that water of 130 degrees is safe under an exposure of 30 seconds, but over that it causes burns. Water of 120 degrees may be safe up to 5 minutes. Hydrogen peroxide (H2O2), when it is exposed to a light of 400-500 nanometers wavelength, may kill 96% of microbes in less than 20 seconds. This solution may work best at 57 degrees Celsius (134 degrees F.).

Alternate embodiments may include heating elements that warm and further super-charge the antimicrobial solution. In embodiments, a device may contain heating or cooling components or both. In an embodiment, an antimicrobial solution may be preheated to an ideal or optimal temperature before it is exposed to synergizing light. For example, Hydrogen peroxide may preferably be exposed to a light of 400-500 nanometers at 57 degrees Celsius (134 degrees F.) for less than 20 seconds. Other chemicals may have different preferred temperatures.

Embodiments of a veterinary device may include integrated or internal heating elements that run adjacent to the light emitting cable in the device. Embodiments of integrated heating elements may be located in only a portion of the device, such as at the bottom of a container or garment. Heating elements may draw power from the same source as the light source, such as batteries or wall power. Power may be supplied to the heating elements in the device through the fiber optic connection cable or through a power connection cable that runs alongside the connection cable.

Alternate embodiments of heating elements may be separate from the portion of the device that retains the antimicrobial solution. Separate heating elements may warm the antimicrobial solution to an optimal temperature before the solution is added to the veterinary device, such as with a heating tray or oven, or may be used to apply heat to the antimicrobial solution in place, such as with a hot iron or wire.

Embodiments of a veterinary device may include a light emitting fiber optic cable that may expose the antimicrobial solution to a certain wavelength of light, such as a purposefully selected wavelength or frequency of light from an LED or laser. A cover for the animal may hold the antimicrobial solution. An embodiment may include a plurality of light terminations or other light emitters on the light emitting fiber optic cable. Each light termination taps into the fiber optic cable to pipe some of the light out the top of the termination, thereby emitting light into the antimicrobial solution. The device may be adjustable, so that the terminations can be added or moved, or the quantity and locations of the light terminations may be measured to fit an individual user. The light terminations may be located within or on the fabric of the cover so that each light termination is will be positioned in a preselected location within the retainer, such as near portions of tissue to be treated. The fiber optic cable may be opaque with light emitters spaced along its length, or may be at least partially translucent to emit light along its length.

In an embodiment, a fiber optic cable may connect to a light source through a fiber optic connection cable. The connection cable may enter the cover and optically connect with the fiber optic cable through a fiber optic connection interface so that the light source can be attached and removed after use. An embodiment of the interface may include a fiber optic connection cable fixed to the fiber optic cable. Another embodiment of the interface may include a socket that mates with a plug on the connection cable so that the light source can be attached and removed after use.

An embodiment may include a veterinary device with a light source and antimicrobial solution. Embodiments may include various animal body or body part coverings.

An embodiment of the present invention may include a veterinary covering for a horse or other quadruped. The covering may be connected to a light source. Embodiments may contain a multitude of fiber optic terminations. Coverings may have a heating element.

Embodiments of an antimicrobial horse blanket may include a cover portion that is shaped to cover the back, shoulders, sides, rear, and possibly the upper legs of a horse or similar animal. A neck portion may cover the animal's neck. A hood portion may cover the animal's face, with openings for the mouth, eyes, and ears. A portion may extend down to cover part of the animal's upper legs. The portions may be integrated as a single piece, or may be in separate portions.

Embodiments of a cover portion may include a nylon sheet, or may include cloth, fleece, or other blanket material. Embodiments of may include straps to releasably hold the front of the cover closed around the horse. The straps may have buckles, buttons, hooks-and-loops, or other fastening elements.

Embodiments of a horse blanket may include a fiber optic cable that wraps around the inside surface the cover. The fiber optic cable may have light terminations spaced along the fiber optic cable inside the cover. An embodiment may include a heating element inside the cover. The heating element may include heating wires inside the cover that run adjacent to the fiber optic cable. The fiber optic cable may connect through a connection cable to a light source. A connection interface or plug may connect and release an external light source from the cover. The heating element may receive power from the light source, through the same light source connection cable or through a separate power connection cable. A switch may allow the light source, the heating power, or both to be connected yet switched on or off.

To use an embodiment, a user may apply antimicrobial solution to the inside of the cover, then wrap the cover around a horse's back and rear. The user may use the straps to close the front of the blanket in front of the horse's neck. If the blanket includes a separate neck or head portion, then the user may also put those portions on the animal and connect the optical or heating wires. The user may turn on the heater or light source or both.

As depicted in the embodiment of FIG. 1, a full horse blanket 10 may include a cover portion 12, a neck portion 14, and an upper legs portion 16. A blanket 10 may include straps 18 to hold the cover closed. The blanket 10 may be coated on the inside with an antimicrobial solution or gel. Embodiments may include a fiber optic cable 20 that wraps around the inside surface the cover portion 12. Embodiments may include a heating element 22, which may include heating wires inside the cover portion 12. Embodiments may include a connection interface 24 that connects the fiber optic cable 20 to a light source 26. Light terminations 28 may be located on the fiber optic cable 20 inside the blanket 10. The light source 26 may have an on/off switch 30 or timer control.

An embodiment of the present invention may include a veterinary medical covering for an animal's head or hooves. The covering may provide a wound healing head and neck protection cover. The covering may be connected to a light source. Embodiments may contain a multitude of fiber optic terminations. Coverings may have a heating element. The cover may be connected to a light source and may have a number of fiber optic light terminators throughout.

Embodiments may be made of soft plastic. Embodiments may adjust for a pet's neck size of 26 to 31 cm, with a depth of about 13 cm. Embodiments may increase the pet's comfort, without damaging the pet's body. Embodiments may be shaped like a truncated cone, and may help prevent the pets from biting its own wound while the wound get itchy after operation, or protect the pets during the skin illness, beauty treatment or medical operation. Embodiments may include a sheet of material in a crescent shape with an attachment mechanism to adjust the length of the neck collar. Embodiments of may include a sheet that folds into the truncated cone shape. The attachment mechanism may include sticky tape or hooks-and-loops at one end to releasably attach the collar to an animal.

Embodiments of an animal cover may include a fiber optic cable that wraps around the inside surface the cover. The fiber optic cable may have light terminations spaced along the fiber optic cable inside the cover. An embodiment may include a heating element inside the cover. The heating element may include heating wires inside the cover that run adjacent to the fiber optic cable. The fiber optic cable may connect through a connection cable to a light source. A connection interface or plug may connect and release an external light source from the cover. The heating element may receive power from the light source, through the same light source connection cable or through a separate power connection cable. A switch may allow the light source, the heating power, or both to be connected yet switched on or off.

As depicted in the embodiment of FIGS. 2A, 2B, and 2C, an animal cover 40 may include a sheet 42 of soft plastic, and an attachment mechanism 44 at one end of the sheet 42. The cover 40 may be wrapped around an animal's neck and the attachment mechanism 44 on one end of the sheet 42 may attach to the other end of the sheet 42 to form a loop. Embodiments may include a soft fabric trim 46 at the top and bottom sides, where the cover 40 rubs against the animal or other objects.

The cover 40 may be coated on the inside with an antimicrobial solution or gel. Embodiments may include a fiber optic cable 48 that wraps around the inside surface the sheet 42. Embodiments may include a heating element 50, which may include heating wires inside the cover. Embodiments may include a connection interface 38 that connects the fiber optic cable 48 to a light source 52. Light terminations 54 may be located on the fiber optic cable 48 inside the blanket. The light source 40 may have an on/off switch 56 or timer control.

To use an embodiment, a user may apply antimicrobial solution to the inside of the cover, then wrap the cover around a animal's neck, hoof, or foot. The user may use the attachment mechanism to close the cover around the animal. For use around the head or neck, the smaller side of the cover may be wrapped around the neck so that the cone and large side of the cover faces outward, protecting the animals head and applying the antimicrobial solution to the animal's neck or head or both. The user may turn on the heater or light source or both.

I claim:

1. A device comprising:
   a solution retainer adapted to retain an antimicrobial solution against an animal;
   a fiber optic cable disposed on a surface of the solution retainer proximate the animal;
   a light termination on the fiber optic cable that provides light from the fiber optic cable to the antimicrobial solution in the solution retainer; and
   a light source that provides a light of a predetermined wavelength to the fiber optic cable.

2. The device of claim 1, wherein the animal is a horse and the solution retainer is a horse blanket.

3. The device of claim 1, further comprising:
   a heating element that warms the antimicrobial solution.

4. The device of claim 1, wherein:
   the solution retainer includes a blanket having a cover portion shaped to cover the back, back, shoulders, sides, and rear of the animal; and
   the fiber optic cable has a plurality of light terminations that emit light from the fiber optic cable to an antimicrobial solution applied to the cover.

5. The device of claim 4, further comprising a neck portion that covers the animal's neck.

6. The device of claim 4, wherein the animal is a horse, and the device further comprises a portion that is shaped to cover the horse's neck.

7. The device of claim 1, wherein the solution retainer includes a sheet made of blanket material and straps with fastening elements to releasably hold the sheet closed around the animal.

8. The device of claim 1, wherein the animal is a quadruped and the solution retainer is a cover for a hoof of the quadruped.

9. The device of claim 1, wherein the light source includes an on/off switch.

10. The device of claim 1, wherein the solution retainer is a cover for a head of the animal.

11. The device of claim 10, further comprising a soft fabric trim along an edge of the cover.

12. The device of claim 10, wherein the cover is a sheet of material that folds into a truncated cone shape.

13. The device of claim 10, further comprising a folding sheet of material and an attachment mechanism adapted to retain the folded sheet in the shape of a truncated cone.

14. A veterinary device comprising:
   a solution retainer including a cover adapted to retain an antimicrobial solution against an animal;
   a fiber optic cable disposed on a surface of the solution retainer proximate the animal;
   a plurality of light terminations on the fiber optic cable that provides light from the fiber optic cable to the antimicrobial solution on the cover;
   a light source that provides a light of a predetermined wavelength to the fiber optic cable; and
   a heating element that warms the antimicrobial solution.

15. The device of claim 4, further comprising:
   a heating element in the cover that heats the antimicrobial solution.

* * * * *